US010338268B2

(12) United States Patent
Chen et al.

(10) Patent No.: US 10,338,268 B2
(45) Date of Patent: Jul. 2, 2019

(54) APPARATUS AND METHOD FOR OBTAINING T2 DISTRIBUTION

(71) Applicant: HALLIBURTON ENERGY SERVICES, INC., Houston, TX (US)

(72) Inventors: Songhua Chen, Katy, TX (US); Wei Shao, Conroe, TX (US)

(73) Assignee: HALLIBURTON ENERGY SERVICES, INC., Houston, TX (US)

( * ) Notice: Subject to any disclaimer, the term of this patent is extended or adjusted under 35 U.S.C. 154(b) by 0 days.

(21) Appl. No.: 15/546,173

(22) PCT Filed: Apr. 14, 2016

(86) PCT No.: PCT/US2016/027505
§ 371 (c)(1),
(2) Date: Jul. 25, 2017

(87) PCT Pub. No.: WO2017/180123
PCT Pub. Date: Oct. 19, 2017

(65) Prior Publication Data
US 2018/0120471 A1    May 3, 2018

(51) Int. Cl.
*G01V 3/32* (2006.01)
*G01R 33/44* (2006.01)
*G01N 24/08* (2006.01)

(52) U.S. Cl.
CPC ............. *G01V 3/32* (2013.01); *G01R 33/448* (2013.01); *G01N 24/081* (2013.01)

(58) Field of Classification Search
CPC .......... G01V 3/32; G01V 3/38; G01R 33/448; G01N 24/081
See application file for complete search history.

(56) References Cited

U.S. PATENT DOCUMENTS

| 6,005,389 A | 12/1999 | Prammer |
| 6,069,477 A | 5/2000 | Chen et al. |

(Continued)

FOREIGN PATENT DOCUMENTS

| EP | 1003053 A2 | 5/2000 |
| WO | 2012037317 A2 | 3/2012 |
| WO | 2015002848 A1 | 1/2015 |

OTHER PUBLICATIONS

International Search Report and Written Opinion; PCT Application No. PCT/US2016/027505; dated Apr. 14, 2016.

(Continued)

*Primary Examiner* — Manuel L Barbee
(74) *Attorney, Agent, or Firm* — Polsinelli PC

(57) ABSTRACT

A method for determining earth formation properties including a data acquisition tool and a data acquisition processor coupled with NMR sensors and a first memory; transmitting earth formation fluid data to a data processing unit comprising a processor and a second memory. Obtaining a fully polarized state echo train ($E_{FR}$) and a partially polarized state echo train burst ($E_{PR}$); inverting the $E_{PR}$ to obtain an apparent transverse relaxation time ($T_{2app}$) distribution; truncating the $T_{2app}$ distribution by discarding the partially polarized state echo train data; completing a forward model of the $E_{PR}$ to obtain an additional echo train burst ($E_{FR\_B}$), performing a second inversion of the data set; and determining earth formation fluid properties.

20 Claims, 5 Drawing Sheets

(56) References Cited

U.S. PATENT DOCUMENTS

| | | |
|---|---|---|
| 8,395,384 B2 | 3/2013 | Fransson et al. |
| 2004/0027122 A1 | 2/2004 | Heaton et al. |
| 2005/0264285 A1* | 12/2005 | Chen ................. G01V 3/32 |
| | | 324/303 |
| 2009/0210159 A1* | 8/2009 | Chen ................. G01V 3/32 |
| | | 702/6 |
| 2013/0214779 A1* | 8/2013 | Tietjen ............... G01V 3/32 |
| | | 324/303 |
| 2016/0320519 A1* | 11/2016 | Blanz ................. G01V 3/32 |

OTHER PUBLICATIONS

Dunn et al., A Method for Inverting Nmr Data Sets With Different Signal to Noise Ratios, SPWLA 39th Annual Logging Symposium, 1998, SPWLA-1998-JJ, Society of Petrophysicists and Well-Log Analysts, Keystone, Colorado.

* cited by examiner ated entry of PCT/US2016/
APPARATUS AND METHOD FOR OBTAINING T2 DISTRIBUTION

CROSS-REFERENCE TO RELATED APPLICATIONS

This application is a national stage entry of PCT/US2016/027505 filed Apr. 14, 2016, said application is expressly incorporated herein in its entirety.

FIELD

The present disclosure generally relates to nuclear magnetic resonance (NMR) well logging. In particular, the subject matter herein generally relates to determining earth formation fluid properties and quantities using a data acquisition tool including one or more NMR sensors.

BACKGROUND

Wellbores are drilled into the earth for a variety of purposes including tapping into hydrocarbon bearing formations to extract hydrocarbons for use as fuel, lubricants, chemical production, and numerous other purposes. In order to facilitate characterization of a subterranean formation and the fluids contained therein, it is often desirable to lower an NMR logging tool into a wellbore.

During various phases of wellbore operations it becomes necessary to identify fluid types and determine the fluid properties of the earth formation where the operations are occurring. Fluid typing and fluid properties can be determined using NMR logging. NMR logging measures the induced magnet moment of hydrogen nuclei contained within fluid-filled pores in porous material, such as rocks. Hydrogen protons primarily occur in pore fluids, such as oil, gas, and water. NMR logs can provide a wide range of information about the fluid, which can be used to determine the rock composition of the earth formation and/or the type and quantity of hydrocarbons within the earth formation.

BRIEF DESCRIPTION OF THE DRAWINGS

Implementations of the present technology will now be described, by way of example only, with reference to the attached figures, wherein.

DETAILED DESCRIPTION

Figure 1A:
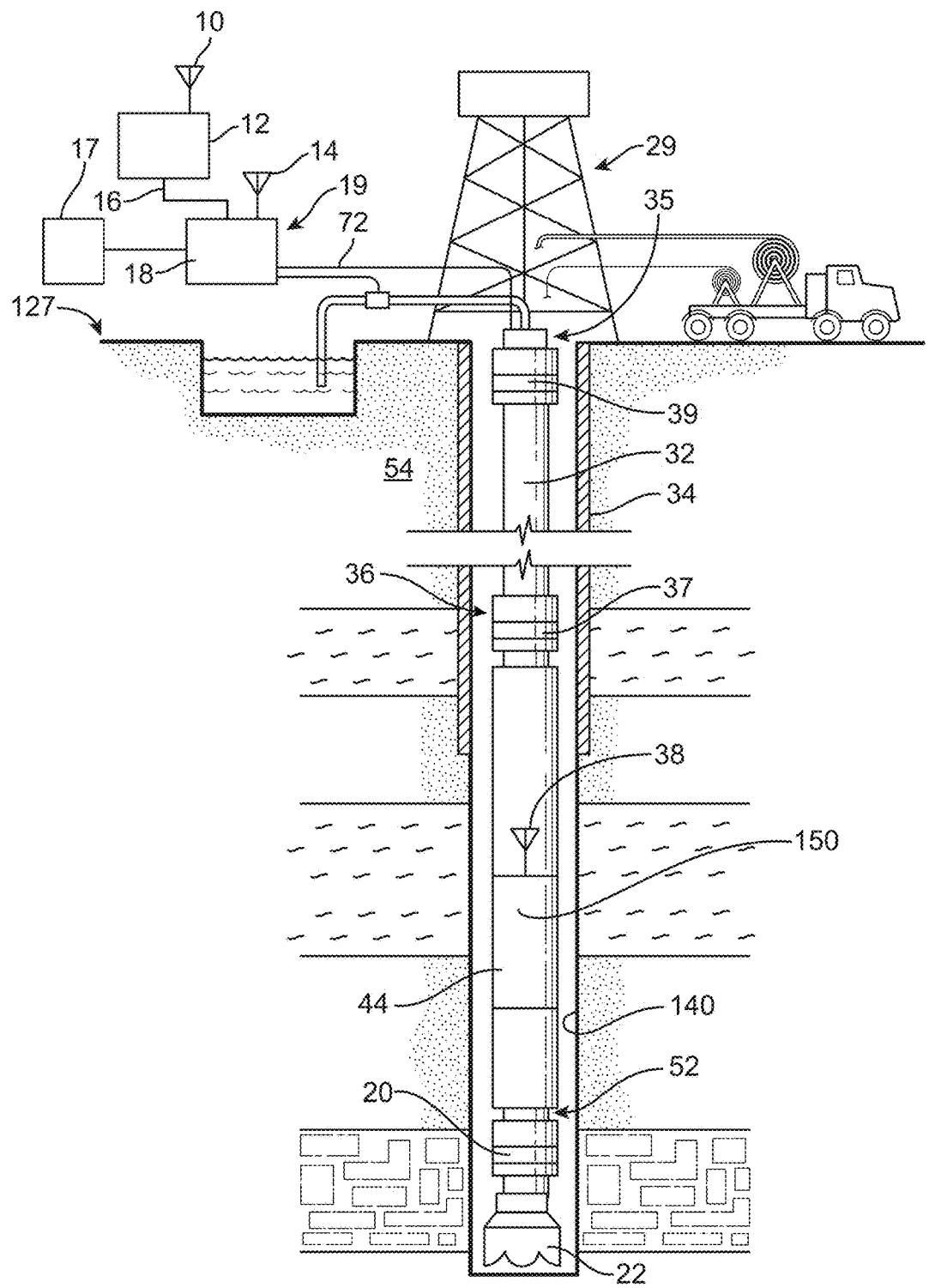
FIG. 1A is a diagram illustrating an exemplary wellbore operating environment in which the downhole logging tool, method, and system may be deployed, according to the disclosure herein.

It will be appreciated that for simplicity and clarity of illustration, where appropriate, reference numerals have been repeated among the different figures to indicate corresponding or analogous elements. In addition, numerous specific details are set forth in order to provide a thorough understanding of the embodiments described herein. However, it will be understood by those of ordinary skill in the art that the embodiments described herein can be practiced without these specific details. In other instances, methods, procedures and components have not been described in detail so as not to obscure the related relevant feature being described. Also, the description is not to be considered as limiting the scope of the embodiments described herein. The drawings are not necessarily to scale and the proportions of certain parts have been exaggerated to better illustrate details and features of the present disclosure.

In the below description, with respect to a wellbore, reference to up or down is made for purposes of description with "up," "upper," "upward," or "uphole" meaning toward the surface of the wellbore and with "down," "lower," "downward," or "downhole" meaning toward the terminal end of the well, regardless of the wellbore orientation.

Several definitions that apply throughout this disclosure will now be presented. The term "coupled" is defined as connected, whether directly or indirectly through intervening components, and is not necessarily limited to physical connections. The connection can be such that the objects are permanently connected or releasably connected. The term "substantially" is defined to be essentially conforming to the particular dimension, shape or other word that substantially modifies, such that the component need not be exact. For example, substantially cylindrical means that the object resembles a cylinder, but can have one or more deviations from a true cylinder. The terms "comprising," "including" and "having" are used interchangeably in this disclosure. The terms "comprising," "including" and "having" mean to include, but not necessarily be limited to, the things so described.

Disclosed herein are an apparatus, a method, and a system for determining fluid properties of an earth formation using a downhole data acquisition tool including one or more nuclear magnetic resonance (NMR) sensors. Data obtained from the NMR sensors can be used to create a mathematical model, for example, an echo train. Information about the fluid properties can be obtained by performing a first inversion of the mathematical model, performing a forward model, and finally performing a second inversion on the data resulting from the forward model.

Logging data acquired by systems as described above can be processed to obtain total porosity information of an earth formation. The longitudinal ($T_1$) and transverse ($T_2$) relaxation time of fluids in rock formations may contain multiple components, which can be shown in the form of a distribution from sub-milliseconds to several seconds. However, components with a short relaxation time rapidly decay. Thus, obtaining an accurate estimation requires the initial echoes to be relatively noise free, which can be difficult to obtain outside a synthetic wellbore. On the other hand, the existence of slow-relaxation components requires a long wait time to allow for spin re-alignment with the external magnetic field (polarization). Spin re-alignment can take 3-5 times the longest T1 component after the previous measurement, the spin polarization is described by Equation 1, $$M(t_w) = M_0 \left[ 1 - e^{-\frac{t_w}{T_1}} \right] \quad (1)$$

where $t_w$ is wait time, M is magnetization along the direction of the magnetic field after spin orientation is destroyed, and $M_0$ is magnetization after polarization is established. Thus, disclosed herein is an improved way to determine porosity information.

NMR logging, as described above, can be conducted during drilling operations in a subterranean well environment as depicted in FIG. 1A. A wellbore 140 is shown that has been drilled into the earth 54 from the ground's surface 127 using a drill bit 22. The drill bit 22 is located at the bottom, distal end of the drill string 32, and the bit 22 and drill string 32 are advanced into the earth 54 by the drilling rig 29. The drilling rig 29 can be supported directly on land as shown or on an intermediate platform (for example, if at sea). For illustrative purposes, the top portion of the wellbore includes casing 34 that can be at least partially made up of cement and defines and stabilizes the wellbore after being drilled. The drill bit 22 can be rotated via rotating the drill string 32, and/or a downhole motor near the drill bit 22.

As shown in FIG. 1A, the drill string 32 supports several components along its length, including a data acquisition tool 150. A sensor sub-unit 52 is shown for detecting conditions near the drill bit 22, conditions can include such properties as formation fluid density, temperature, pressure, and azimuthal orientation of the drill bit 22 or string 32. Measurement while drilling (MWD)/logging while drilling (LWD) procedures are supported both structurally and communicatively, which can include the NMR logging operations as discussed herein. The instance of directional drilling is illustrated in FIG. 1A. The lower end portion of the drill string 32 can include a drill collar proximate the drilling bit 22 and a drilling device such as a rotary steerable drilling device 20, or other drilling devices disclosed herein. The drill bit 22 may take the form of a roller cone bit or fixed cutter bit or any other type of bit known in the art. The sensor sub-unit 52 is located in or proximate to the rotary steerable drilling device 20 and advantageously detects the azimuthal orientation of the rotary steerable drilling device 20. Other sensor sub-units 35, 36 are shown within the cased portion of the well which can be enabled to sense nearby characteristics and conditions of the drill string, formation fluid, casing and surrounding formation. Regardless of which conditions or characteristics are sensed, data indicative of those conditions and characteristics is either recorded downhole, for instance at the processor 44 for later download, or communicated to the surface either by wire using repeaters 37, 39 up to surface wire 72, or wirelessly, or otherwise. If wirelessly, a downhole transceiver (antenna) 38 can be utilized to send data to a local processor 18, via topside transceiver (antenna) 14. There the data may be either processed or further transmitted along to a remote processor 12 via wire 16 or wirelessly via antennae 14 and 10.

A surface installation 19 is shown that sends and receives data to and from the well. The surface installation 19 can include a local processor 18 that can optionally communicate with one or more remote processors 12, 17 by wire 16 or wirelessly using transceivers 10, 14.

The exemplary rotary steerable drilling device 20, shown in FIG. 1A, can also be referred to as a drilling direction control device or system. As shown, the rotary drilling device 20 is positioned on the drill string 32 with drill bit 22. However, one of skill in the art will recognize that the positioning of the rotary steerable drilling device 20 on the drill string 22 and relative to other components on the drill string 22 may be modified while remaining within the scope of the present disclosure.

Figure 1B:
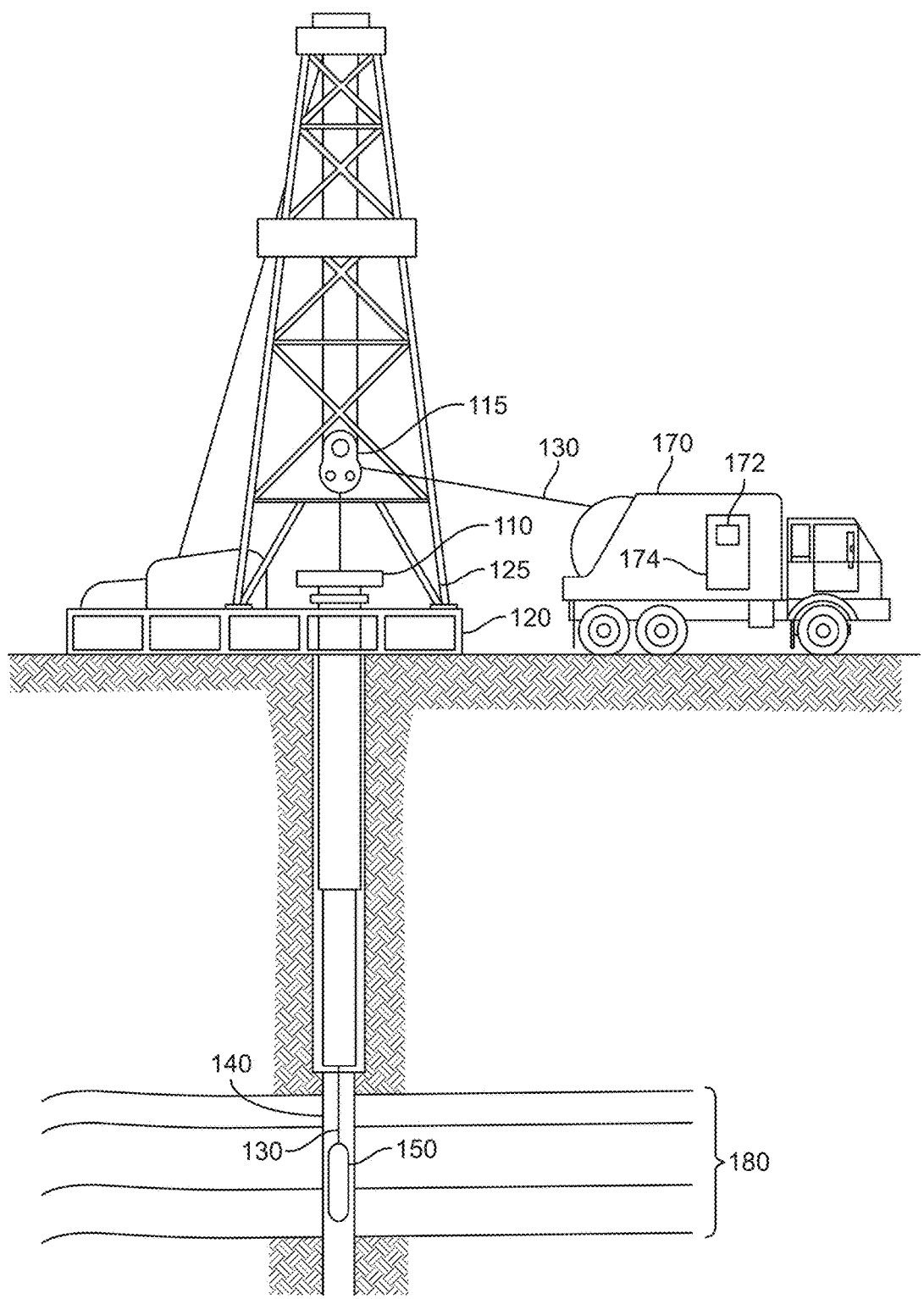
FIG. 1B is a diagram illustrating a second exemplary wellbore operating environment in which the downhole logging tool, method, and system may be deployed, according to the disclosure herein.

FIG. 1B illustrates a system 100 according to various embodiments of the present disclosure. As described above, the data acquisition tool 150 can be used as part of a wireline logging operation, or as part of a downhole drilling operation. For example, FIG. 1B shows a well during wireline logging operations. A drilling platform 120 may be equipped with a derrick 125 that supports a hoist 115. Drilling oil and gas wells can be carried out using a string of drill pipes connected together so as to form a drilling string that is lowered through a rotary table 110 into a wellbore, or borehole, 140.

Here it is assumed that the drilling string has been temporarily removed from the wellbore 140 to allow a data acquisition tool 150 to be lowered by wireline or logging cable 130 into the wellbore 140. The data acquisition tool 150 can be lowered to a desired location and pulled upward at a substantially constant speed. As the data acquisition tool 150 is pulled upward, instruments included in the tool 150 (for example, NMR sensors) may be used to perform measurements on subsurface formations 180 adjacent to the wellbore 140. The measurement data can include a plurality of echo trains and can be transmitted to a logging facility 170 for storage, processing, and analysis. The logging facility 170 can include electronic equipment for various types of signal processing. For example, the logging facility 170 may include one or more surface computers 174 and one or more displays 172. In the alternative, the data can be processed off-site.

Although FIGS. 1A and 1B depict a vertical wellbore 140, the present disclosure is equally well-suited for use in wellbores having other orientations, including horizontal wellbores, slanted wellbores, multilateral wellbores or the like. It should be noted that while FIGS. 1A and 1B generally depict land-based operations, those skilled in the art would readily recognize that the principles described herein are equally applicable to operations that employ floating or sea-based platforms and rigs, without departing form the scope of the disclosure.

Furthermore, although FIGS. 1A and 1B show exemplary environments relating to NMR logging in the absence, or temporary cessation, of drilling operations and LWD operations, the present disclosure is equally well-suited to the characterization of core samples brought to the surface from subterranean formations. As such, the present disclosure is equally well-suited in the use of core analysis equipment for the characterization of core samples in a laboratory or surface environment.

Figure 2:
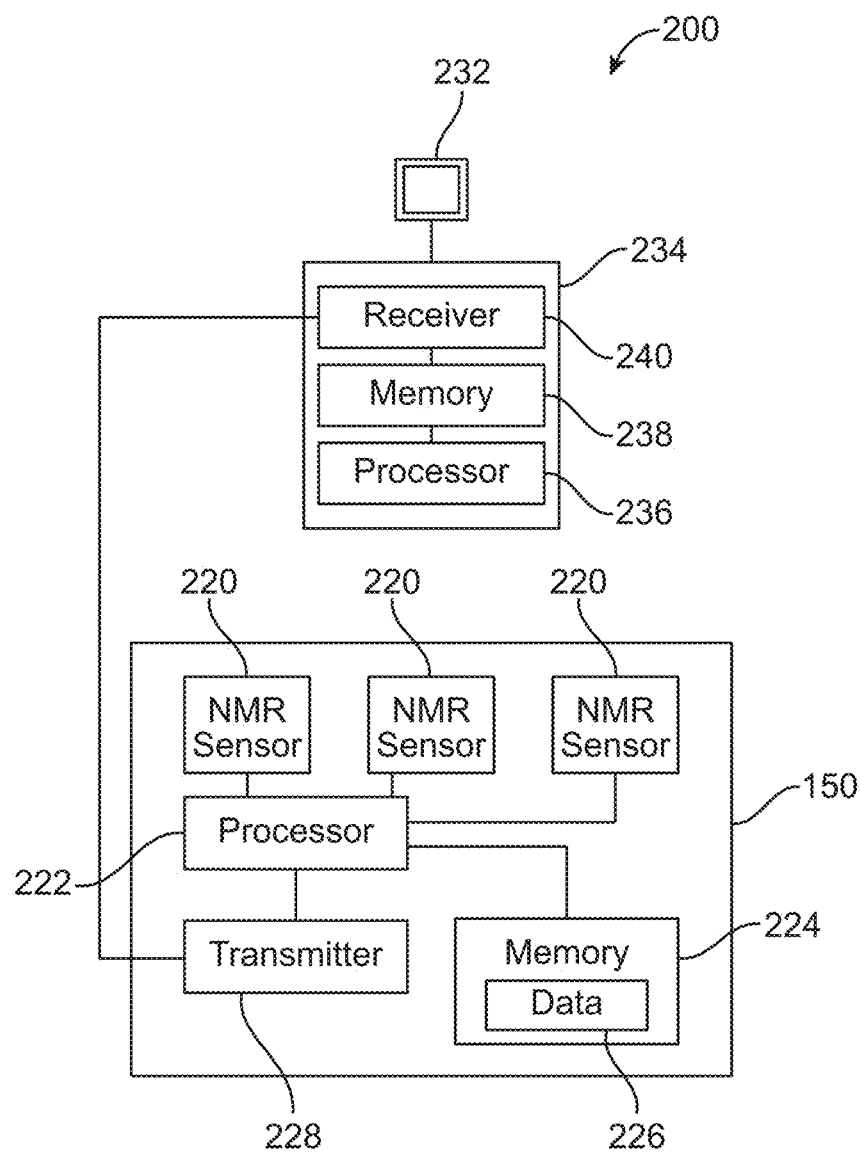
FIG. 2 is a diagram illustrating an apparatus according to the disclosure herein.

A variety of apparatuses, systems, and methods may be used to implement the activities described above. For example, FIG. 2 illustrates an apparatus 200 according to various embodiments of the present disclosure.

In some embodiments, the apparatus 200 may include a data acquisition tool 150 to acquire fluid signature data 226 associated with fluids in a material, such as a geologic formation. In addition, the data acquisition tool 150 may include one or more NMR sensors 220 and at least one memory 224 to store the fluid signature data 226. The data acquisition tool 150 may also include a processor 222, to constrain ratios of $T_1$ relaxation times to $T_2$ relaxation times, and a transmitter 228, to transmit the fluid signature data 226.

The apparatus 200 can further include a data processing unit 234. The data processing unit 234 can be located above-ground. In the alternative, the data processing unit can be downhole, for example, when using LWD or slickline tools. The data processing unit 234 can be communicatively coupled with a receiver 240 to receive transmitted fluid signature data 226. The data processing unit 234 can further include a processor 236 and a memory 238, and can be coupled with a display 232. The display 232 may be used to display the location of a fluid type (e.g., water, gas, and/or oil) based on the fluid properties determined from the collected fluid signature data 226.

The data obtained by the apparatus and systems described above can be used to create a $T_2$ distribution, as well as porosity information regarding the earth formations drilled. Several methods can be used. A typical NMR data logging method can include the use of at least two echo trains, a long, fully polarized echo train and a partially polarized short echo burst, containing a substantially smaller number of echoes, to determine total porosity. High levels of noise within the NMR data can create significant interference in the resulting porosity information. Thus, the use of a long, fully polarized echo train and one or more partially polarized echo train bursts allow for adequate signal-to-noise ratio (SNR) for recovering both the long and short $T_2$ components. The fully-polarized (FR) long echo train and the low-noise, partially polarized (PR) echo train bursts can then be processed to obtain a single $T_2$ distribution. In order to account for the polarization effect, Equation 2 can be used.

$$E(i,j,k) = \sum_{m=1}^{M} \sum_{n=1}^{N} E_{0,mn} \left[1 - e^{-\frac{t_{W_k}}{T_{1,m}}}\right] e^{-i\frac{t_{E_j}}{T_{2,n}}} \quad (2)$$

In the FR echo train, the parameter $$\left[1 - e^{-\frac{t_{W_k}}{T_{1,m}}}\right] = 1$$

for all components, thus, Eqn. 2 can be simplified to Equation 3, shown below.

$$E_{FR}(i,j,t_{W_{FR}}) = \sum_{m=1}^{M} E_{0,m} e^{-i\frac{t_{E_j}}{T_{2,m}}} \quad (3)$$

However, in the PR echo train bursts, only the fast decay components (m=1, ..., μ) can satisfy the parameter $$\left[1 - e^{-\frac{t_{W_{PR}}}{T_{1,m}}}\right] = 1.$$

Assuming the same number of bins for $T_1$ and $T_2$, the parameter $R \equiv T_1/T_2$ can be used, resulting in Equation 4, $$E(i,j,k) = \sum_{n=1}^{\mu} E_{0,n} e^{-i\frac{t_{E_j}}{T_{2,n}}} + \sum_{n=\mu+1}^{N} E_{0,n} \left[1 - e^{-\frac{t_{W_k,PR}}{T_{2,n}}}\right] e^{-i\frac{t_{E_j}}{T_{2,n}}} \quad (4)$$

wherein the first term $$\sum_{n=1}^{\mu} E_{0,n} e^{-i\frac{t_{E_j}}{T_{2,n}}}$$

represents the fully polarized components and the second term $$\sum_{n=\mu+1}^{N} E_{0,n} \left[1 - e^{-\frac{t_{W_k,PR}}{T_{2,n}}}\right] e^{-i\frac{t_{E_j}}{T_{2,n}}}$$

represents the partially polarized components. The ratio parameter, $R_n$, can be different for different components (n). However, the n-dependent ratio parameter ($R_n$) does not simplify the inversion algorithm compared to directly inverting for $T_{1,n}$ and $T_{2,n}$. Simplification can occur through the approximation of $R_n$ as a constant for all components. Such simplification allows the long $T_{2,n}$ components to contribute less to the PR echo bursts as n increases. In an alternative approach, the $R_n$ constraint can be relaxed. However, the estimation of R as described in the above simplifications can decrease the accuracy of the resulting information.

Furthermore, while the use of various $t_w$ echoes is essential for an accurate $T_1$ estimation, the method, as described above, does not utilize each of the obtained shorter $t_w$ echo trains, resulting a in less accurate $T_2$ inversion. Thus, multiple $t_{W_{PR}}$ PR burst echo trains can be used in order to improve the quality of the $T_2$ inversion.

For example, the $T_2$ distribution and porosity information can be obtained using at least one substantially FR echo train, obtained using Eqn. 3, and at least one PR burst echo train, obtained using Eqn. 2, as follows. For the purposes of illustration, a system is assumed wherein a single $E_{FR}$ echo train and two $E_{PR}$ burst echo trains are obtained.

The two $E_{PR}$ burst echo trains are obtained using the following Equations. The first burst echo train, $E_{PR1}$, is obtained using Equation 6.

$$E_{PR1}(i, t_{E_1}, t_{W_1}) = \sum_{n=1}^{\mu} E_{0,n} e^{-i\frac{t_{E_1}}{T_{2,n}}} + \sum_{n=\mu+1}^{N} E_{0,n} \left[1 - e^{-\frac{t_{W_1}}{T_{1,n}}}\right] e^{-i\frac{t_{E_1}}{T_{2,n}}} \quad (6)$$

A one-dimensional (1D) inversion is performed, wherein the parameter $$E_{0,n} \left[1 - e^{-\frac{t_{W_1}}{T_{1,n}}}\right]$$

can be symbolically written as $E'_{0,n}$, representing all of the partially polarized bin porosities. The result of the substitution is shown in Equation 7.

$$E_{PR1}(i, t_{E_1}, t_{W_1}) = \sum_{n=1}^{\mu} E_{0,n} e^{-i\frac{t_{E_1}}{T_{2,n}}} + \sum_{n=\mu+1}^{N} E'_{0,n} e^{-i\frac{t_{E_1}}{T_{2,n}}} \quad (7)$$

The second burst echo train, $E_{PR2}$, is similarly obtained using Equation 8.

$$E_{PR2}(i, t_{E_2}, t_{W_2}) = \sum_{n=1}^{v} E_{0,n} e^{-i\frac{t_{E_2}}{T_{2,n}}} + \sum_{n=v+1}^{N} E'_{0,n} e^{-i\frac{t_{E_2}}{T_{2,n}}} \quad (8)$$

An inversion of $E_{PR1}$ is completed using Eqn. 7, retaining only the fully polarized bins (n=1, ..., μ) to generate a new burst echo train $E_{FP\_B1}$, which contains only fully polarized bins, as described by Equation 9, $$E_{FP\_B1}(i, t_{E_1}, t_{W_1}) = \sum_{n=1}^{\mu} E_{0,n,est} e^{-i\frac{t_{E_1}}{T_{2,n}}} \quad (9)$$

where $E_{0,n,est}$ is the estimated bin porosity corresponding to $T_{2,n}$.

An inversion of $E_{PR2}$ is similarly performed using Eqn. 8, retaining only the fully polarized bins (n=1, ..., v) and generating a new burst echo train $E_{FP\_B2}$ with only fully polarized bins, as described by Equation 10, $$E_{FP\_B2}(i, t_{E_2}, t_{W_2}) = \sum_{n=1}^{v} E_{0,n,est} e^{-i\frac{t_{E_2}}{T_{2,n}}} \quad (10)$$

where $E_{0,n,est}$ is the estimated bin porosity corresponding to $T_{2,n}$.

Eqns. 3, 9, and 10 can then be inverted together to obtain a $T_2$ distribution and total porosity information of the earth formation, using only fully polarized echo data. Assuming, for the purposes of this illustration, the $E_{FR}$ echo train has N echoes, $E_{FR\_B1}$ burst has $N_1$ echoes, and $E_{FR\_B2}$ burst has $N_2$ echoes. Eqns. 3, 9 and 10 can then be combined in matrix notation E=Ax, where A is a $N_1+N_2+N$ by M matrix, as shown in Equation 11.

$$A = \begin{bmatrix} e^{-t_E/T_{21}} & e^{-t_E/T_{22}} & \ldots & e^{-t_E/T_{2\mu}} & 0 & \ldots & \ldots & \ldots & 0 \\ \vdots & \vdots & \vdots & \vdots & \vdots & \ldots & \vdots & \vdots & \vdots \\ e^{-N_1 t_E/T_{21}} & e^{-N_1 t_E/T_{22}} & \ldots & e^{-N_1 t_E/T_{2\mu}} & 0 & \ldots & \ldots & \ldots & 0 \\ e^{-t_E/T_{21}} & e^{-t_E/T_{22}} & \ldots & \ldots & \ldots & e^{-t_E/T_{2v}} & 0 & \ldots & 0 \\ \vdots & \vdots & \vdots & \vdots & \vdots & \vdots & \vdots & \vdots & \vdots \\ e^{-N_2 t_E/T_{21}} & e^{-N_2 t_E/T_{22}} & \ldots & \ldots & \ldots & e^{-N_2 t_E/T_{2v}} & 0 & \ldots & 0 \\ e^{-t_E/T_{21}} & e^{-t_E/T_{22}} & \ldots & \ldots & \ldots & \ldots & \ldots & \ldots & e^{-t_E/T_{2M}} \\ \vdots & \vdots & \vdots & \vdots & \vdots & \vdots & \vdots & \vdots & \vdots \\ e^{-N t_E/T_{21}} & e^{-N t_E/T_{22}} & \ldots & \ldots & \ldots & \ldots & \ldots & \ldots & e^{-N t_E/T_{2M}} \end{bmatrix} \quad (11)$$

x solution to vector of M elements:

$$x = \begin{bmatrix} E_{01} \\ \vdots \\ E_{0M} \end{bmatrix}$$

where E contains the originally acquired $E_{FP}$ echoes and the polarization-corrected $E_{FP\_B1}$ and $E_{FP\_B2}$ bursts:

$$E = \begin{bmatrix} E_{FR\_B1(1)} \\ \vdots \\ E_{FR\_B1(N_1)} \\ E_{FR\_B2(1)} \\ \vdots \\ E_{FR\_B1(N_2)} \\ E_{FR(1)} \\ \vdots \\ E_{FR(N)} \end{bmatrix}$$

The $t_{E1}$ and $t_{E2}$ of $E_{FP\_B1}$ and $E_{FP\_B2}$ can be the same as the originally acquired $E_{PR1}$ and $E_{PR2}$. In the alternative, if the $t_{E1}$ and $t_{E2}$ values of $E_{FP\_B1}$ and $E_{FP\_B2}$ are different from the originally acquired $t_E$ value of $E_{FP}$, the forward model of $E_{FP\_B1}$ and $E_{FP\_B2}$ can be performed using the $t_E$ value of $E_{FP}$.

The number of forward modeled $E_{FP\_B1}$ and $E_{FP\_B2}$ echoes ($N_1$ and $N_2$, respectively) can be the same as the number as originally acquired in echo bursts $E_{PR1}$ and $E_{PR2}$. In the alternative, the number of echoes can be selected based on the amplitude of either $E_{FP\_B1}$ or $E_{FP\_B2}$. For example, if the amplitude of the forward modeled $l^{th}$ echo is comparable to the uncertainty level, the forward modeled echo train can terminate at the $l^{th}$ echo.

In a second illustrative example, at least one substantially FR echo train, as described by Eqn. 3 and at least one PR burst echo train as described by Eqn. 2 are obtained. It is assumed, for the purposes of this example, that two PR burst echo trains are obtained. The two PR burst echo trains are described as follows.

The first burst echo train, $E_{PR1}$, can be obtained using Equation 12.

$$E_{PR1}(i, t_{E_1}, t_{W_1}) = \sum_{n=1}^{\mu} E_{0,n} e^{-i\frac{t_{E_1}}{T_{2,n}}} + \sum_{n=\mu+1}^{N} E'_{0,n} e^{-i\frac{t_{E_1}}{T_{2,n}}} \quad (12)$$

The second burst echo train, $E_{PR2}$, can be similarly obtained using Equation 13.

$$E_{PR2}(i, t_{E_2}, t_{W_2}) = \sum_{n=1}^{v} E_{0,n} e^{-i\frac{t_{E_1}}{T_{2,n}}} + \sum_{n=v+1}^{N} E'_{0,n} e^{-i\frac{t_{E_1}}{T_{2,n}}} \quad (13)$$

A first inversion of $E_{PR1}$ is completed using Eqn. 12 and retaining only the fully polarized bins (n=1, . . . , μ). A new burst echo train $E_{FR\_B1}$ is generated having only fully polarized bins, represented by Equation 14, $$E_{FR\_B1}(i, t_{E_1}, t_{W_1}) = \sum_{n=1}^{\mu} E_{0,n,est} e^{-i\frac{t_{E_2}}{T_{2,n}}} \quad (14)$$

wherein $E_{0,n,est}$ is the estimated bin porosity corresponding to $T_{2,n}$.

A second inversion of $E_{FP\_B1}$ and $E_{PR2}$ echo trains can be performed, using Eqns. 3 and 11, respectively, and retaining only the fully polarized bins (n=1, . . . , v). A new burst echo train $E_{FP\_B2}$ is generated, as described by Equation 15, $$E_{FP\_B2}(i, t_{E_2}, t_{W_2}) = \sum_{n=1}^{v} E_{0,n,est} e^{-i\frac{t_{E_2}}{T_{2,n}}} \quad (15)$$

wherein $E_{0,n,est}$ is the estimated bin porosity corresponding to $T_{2,n}$.

Finally, Eqns. 3, 13 and 14 can be inverted together to obtain a $T_2$ distribution and total porosity information of the earth formation, using only fully polarized echo data.

Figure 3:
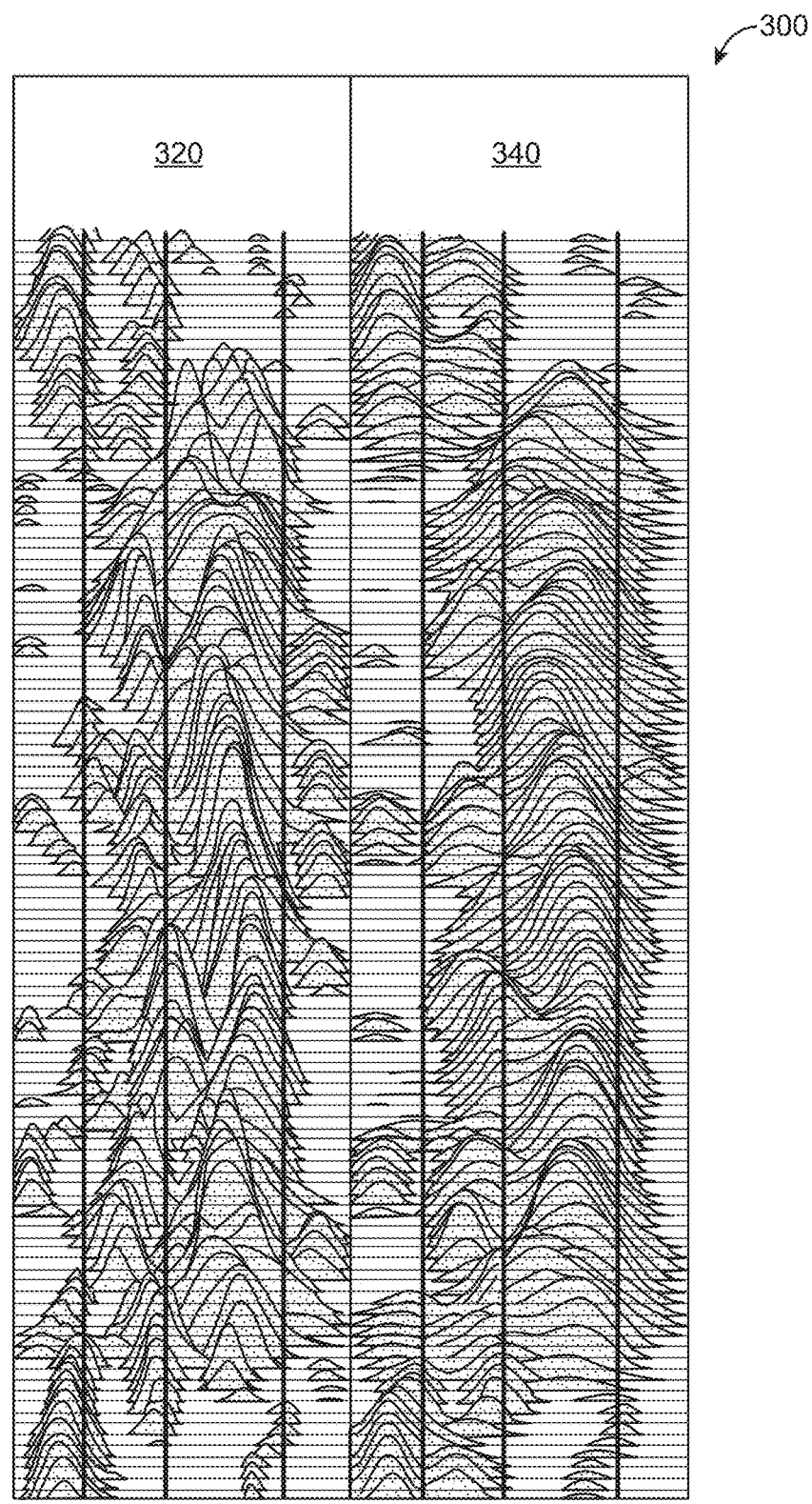
FIG. 3 is a diagrammatic view of a $T_2$ distribution comparison of a synthetic carbonate reservoir section.
Figure 4:
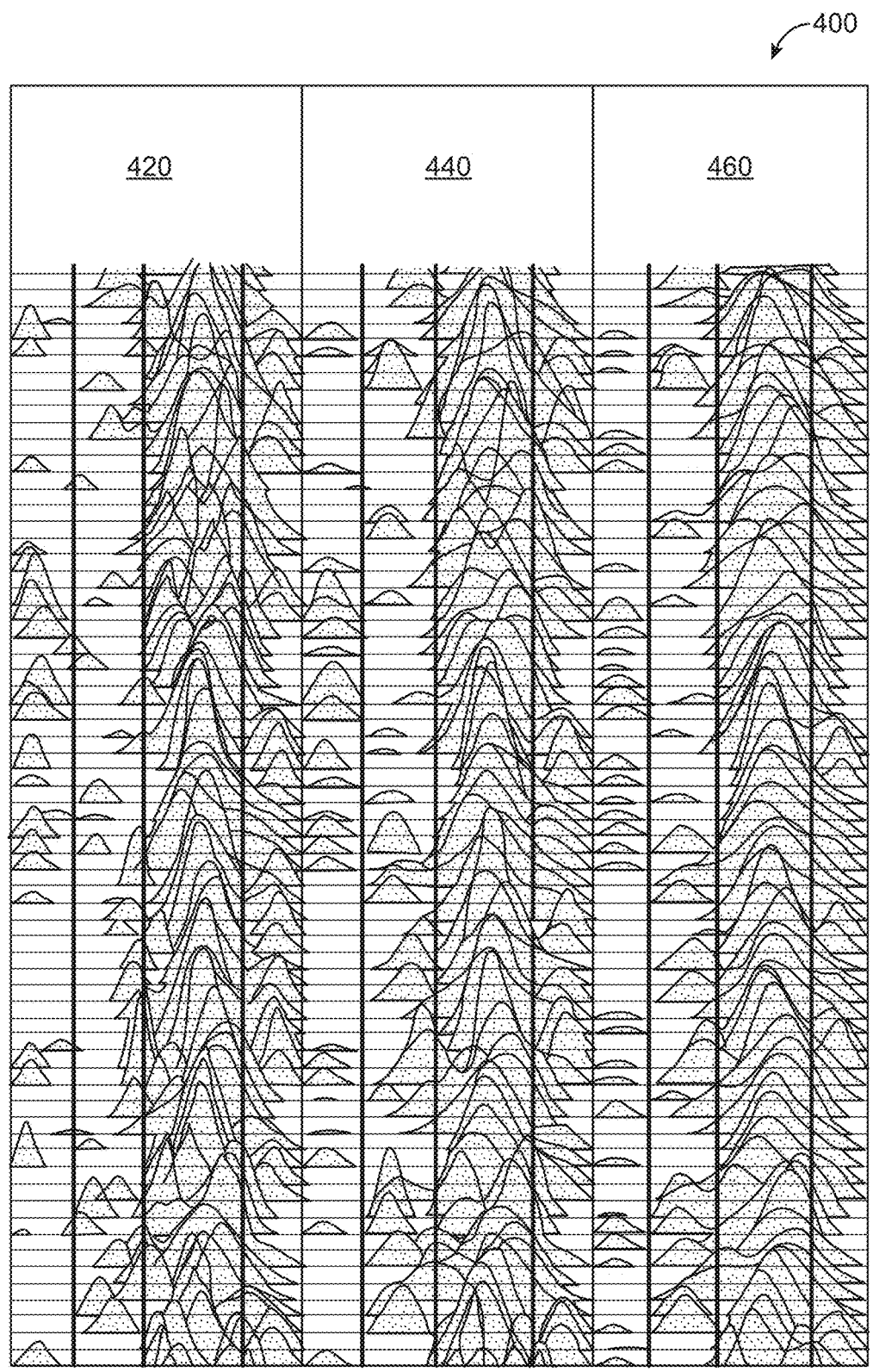
FIG. 4 is a diagrammatic view of a second $T_2$ distribution comparison of a synthetic carbonate reservoir section.

The results of the above described methods can be illustrated by the $T_2$ distribution of carbonate reservoirs, as shown in FIGS. 3 and 4. FIG. 3 illustrates a comparison 300 of the $T_2$ distribution results from a carbonate reservoir obtained using a first method 320 and a second method 340. The first method 320 was performed using a single $T_1/T_2$ ratio parameter, estimated from a single FR echo train and a single PR echo train. Conversely, the second method 340 was performed using a single PR echo train inverted to obtain an echo train burst having only fully polarized components, and subsequently inverting the PR echo train, echo train burst, and a single FR echo train. As shown, the second method 340 provides a more accurate $T_2$ distribution, as indicated by the more uniform distribution of peaks.

FIG. 4 illustrates a second comparison 400 of the $T_2$ distribution results from a carbonate reservoir obtained using a first method 420, a second method 440, and a third method 460. The first method 420 and second method 440 were performed in substantially the same manner as the first method 320 and the second method 340 described above, respectively. The third method 460 was performed in substantially the same manner as the second method 440, however, two PR echo trains were used rather than one. As discussed above with respect to FIG. 3, the calculations which include the shorter $t_w$ echo train data result in a significantly more uniform $T_2$ distribution than those without. Furthermore, the method 460 which used a larger number of PR echo trains shows an even more uniform $T_2$ distribution.

Numerous examples are provided herein to enhance understanding of the present disclosure. A specific set of statements are provided as follows.

Statement 1: A method for determining earth formation rock and fluid properties comprising providing a data acquisition tool, the data acquisition tool comprising one or more NMR sensors, a data acquisition processor communicatively coupled with the one or more NMR sensors, and a first memory communicatively coupled with the data acquisition processor; lowering the data acquisition tool to a desired location within a wellbore; receiving, at the data acquisition tool, data of earth formation fluid; transmitting the acquired data to a data processing unit communicatively coupled with the data acquisition tool, the data processing unit comprising a data processor and a second memory; obtaining, from the acquired data, at least one fully polarized state echo train ($E_{FR}$) and at least one partially polarized state echo train burst ($E_{PR}$), wherein the at least one $E_{PR}$ includes a plurality of partially polarized bins and a plurality of fully polarized bins; inverting the at least one $E_{PR}$ to obtain an apparent transverse relaxation time ($T_{2app}$) distribution, wherein the $T_{2app}$ distribution includes fully polarized state echo train data and partially polarized state echo train data; truncating the $T_{2app}$ distribution by discarding the partially polarized state echo train data; completing a forward model of the $E_{PR}$ to obtain at least one additional echo train burst ($E_{FR\_B}$); performing a second inversion of the data set; determining, at the data processor, earth formation fluid properties based on the second inversion.

Statement 2: A method is disclosed according to Statement 1, wherein the earth formation fluid properties are used to determine one of a bound water location, a movable water location, a fluid type, or a fluid volume.

Statement 3: A method is disclosed according to Statement 1 or Statement 2, wherein the at least one $E_{FR}$ is obtained by the following equation:

$$E_{FR}(i, t_E, t_{W_{FR}}) = \sum_{m=1}^{M} E_{0,m} e^{-i\frac{t_{E_j}}{T_{2,m}}}.$$

Statement 4: A method is disclosed according to Statements 1-3, wherein the at least one $E_{PR}$ is obtained by the following equation:

$$E_{PR}(i, t_E, t_W) = \sum_{n=1}^{\mu} E_{0,n} e^{-i\frac{t_E}{T_{2,n}}} + \sum_{n=\mu+1}^{N} E'_{0,n} e^{-i\frac{t_E}{T_{2,n}}}$$

where μ is a number of fully polarized bins.

Statement 5: A method is disclosed according to Statements 1-4, wherein completing the forward model further comprises generating at least one $E_{FR\_B}$ having only fully polarized bins using the following equation:

$$E_{FP\_B}(i, t_E, t_W) = \sum_{n=1}^{\mu} E_{0,n,est} e^{-i\frac{t_E}{T_{2,n}}}$$

where $E_{0,n,est}$ is the estimated bin porosity corresponding to $T_{2,n}$.

Statement 6: A method is disclosed according to Statements 1-5, wherein the second inversion further comprises inverting the at least one $E_{FR}$ and the at least one $E_{FR\_B}$ simultaneously to obtain a $T_2$ distribution and a total porosity level.

Statement 7: A method is disclosed according to Statements 1-5, wherein two or more $E_{FR\_B}$ are obtained, and wherein the second inversion further comprises inverting the at least one $E_{FR}$ and the two or more $E_{FR\_B}$ sequentially to obtain a $T_2$ distribution and a total porosity level.

Statement 8: A method is disclosed according to Statements 1-7, wherein when more than one $E_{FR\_B}$ is obtained, each $E_{FR\_B}$ is forward modeled independently and the second inversion is applied to $E_{FR}$ and each $E_{FR\_B}$ concurrently.

Statement 9: A method is disclosed according to Statements 1-8, wherein the wait time ($t_w$) of the at least one $E_{PR}$ is shorter than the $t_w$ of the at least one $E_{FR}$.

Statement 10: A method is disclosed according to Statements 1-9, wherein the at least one $E_{PR}$ has a first number of echoes and the at least one $E_{FR}$ has a second number of echoes, wherein the second number of echoes is greater than the first number of echoes.

Statement 11: A method is disclosed according to Statements 1-10, wherein the at least one $E_{FR\_B}$ has the same number of echoes as the at least one $E_{PR}$.

Statement 12: A method is disclosed according to Statements 1-10, wherein the at least one $E_{FR\_B}$ has a different number of echoes than the at least one $E_{PR}$.

Statement 13: A method is disclosed according to Statements 1-12, wherein the at least one $E_{FR\_B}$ has the same $t_E$ value as the at least one $E_{PR}$.

Statement 14: A method is disclosed according to Statements 1-12, wherein the at least one $E_{FR\_B}$ has a different $t_E$ value than the at least one $E_{PR}$.

Statement 15: A method is disclosed according to Statements 1-14, further comprising displaying the earth formation fluid properties on a display screen communicatively coupled with the data processing unit.

Statement 16: A system comprising a data acquisition tool disposed in a wellbore, the data acquisition tool comprising one or more NMR sensors communicatively coupled to a data acquisition processor, and a first memory communicatively coupled to the data acquisition processor, the first memory storing instructions that, when executed by the data acquisition processor, cause the data acquisition processor to perform operations comprising receiving, at the data acquisition tool, data of earth formation fluid, and transmitting, at the data acquisition processor, the acquired data; a data processing unit communicatively coupled with the data acquisition tool, the data processing unit comprising a second memory storing instructions that, when executed by a data processor, cause the data processor to perform operations comprising receiving, from the data acquisition processor, the acquired data, obtaining, from the acquired data, at least one fully polarized state echo train ($E_{FR}$) and at least one partially polarized state echo train burst ($E_{PR}$), wherein the at least one $E_{PR}$ includes a plurality of partially polarized bins and a plurality of fully polarized bins, inverting the at least one $E_{PR}$ to obtain an apparent transverse relaxation time ($T_{2app}$) distribution, wherein the $T_{2app}$ distribution includes fully polarized state echo train data and partially polarized state echo train data, truncating the $T_{2app}$ distribution by discarding the partially polarized state echo train data, completing a forward model of the $E_{PR}$ to obtain at least one additional echo train burst ($E_{FR\_B}$), performing a second inversion of the data set, and determining, at the data processor, earth formation fluid properties based on the second inversion.

Statement 17: A system is disclosed according to Statement 16, wherein the earth formation fluid properties are used to determine one of a bound water location, a movable water location, a fluid type, or a fluid volume.

Statement 18: A system is disclosed according to Statement 16 or Statement 17, wherein the at least one $E_{FR}$ is obtained by the following equation:

$$E_{FR}(i, t_E, t_{W_{FR}}) = \sum_{m=1}^{M} E_{0,m} e^{-i\frac{t_{E_j}}{T_{2,m}}}.$$

Statement 19: A system is disclosed according to Statement 16-18, wherein the at least one $E_{PR}$ is obtained by the following equation:

$$E_{PR}(i, t_E, t_W) = \sum_{n=1}^{\mu} E_{0,n} e^{-i\frac{t_E}{T_{2,n}}} + \sum_{n=\mu+1}^{N} E'_{0,n} e^{-i\frac{t_E}{T_{2,n}}}$$

where $\mu$ is a number of fully polarized bins.

Statement 20: A system is disclosed according to Statements 16-19, wherein completing the forward model further comprises generating at least one $E_{FR\_B}$ having only fully polarized bins using the following equation:

$$E_{FP\_B}(i, t_E, t_W) = \sum_{n=1}^{\mu} E_{0,n,est} e^{-i\frac{t_E}{T_{2,n}}}$$

where $E_{0,n,est}$ is the estimated bin porosity corresponding to $T_{2,n}$.

Statement 21: A system is disclosed according to Statements 16-20, wherein the second inversion further comprises inverting the at least one $E_{FR}$ and the at least one $E_{FR\_B}$ simultaneously to obtain a $T_2$ distribution and a total porosity level.

Statement 22: A system is disclosed according to Statements 16-21, wherein two or more $E_{FR\_B}$ are obtained, and wherein the second inversion further comprises inverting the at least one $E_{FR}$ and the two or more $E_{FR\_B}$ sequentially to obtain a $T_2$ distribution and a total porosity level.

Statement 23: A system is disclosed according to Statements 16-22, wherein when more than one $E_{FR\_B}$ is obtained, each $E_{FR\_B}$ is forward modeled independently and the second inversion is applied to $E_{FR}$ and each $E_{FR\_B}$ concurrently.

Statement 24: A system is disclosed according to Statements 16-23, wherein the wait time ($t_w$) of the at least one $E_{PR}$ is shorter than the $t_w$ of the at least one $E_{FR}$.

Statement 25: A system is disclosed according to Statements 16-24, wherein the at least one $E_{PR}$ has a first number of echoes and the at least one $E_{FR}$ has a second number of echoes, wherein the second number of echoes is greater than the first number of echoes.

Statement 26: A system is disclosed according to Statements 16-25, wherein the at least one $E_{FR\_B}$ has the same number of echoes as the at least one $E_{PR}$.

Statement 27: A system is disclosed according to Statements 16-25, wherein the at least one $E_{FR\_B}$ has a different number of echoes than the at least one $E_{PR}$.

Statement 28: A system is disclosed according to Statements 16-27, wherein the at least one $E_{FR\_B}$ has the same $t_E$ value as the at least one $E_{PR}$.

Statement 29: A system is disclosed according to Statements 16-27, wherein the at least one $E_{FR\_B}$ has a different $t_E$ value than the at least one $E_{PR}$.

Statement 30: A system is disclosed according to Statements 16-29, further comprising a display communicatively coupled to the data processing unit and rendering the determined earth formation fluid properties.

Statement 31: An apparatus comprising a data acquisition tool comprising one or more NMR sensors; a data acquisition processor communicatively coupled with the one or more NMR sensors; and a first memory storing instructions that, when executed by the data acquisition processor, cause the data acquisition processor to perform operations comprising acquiring, at the one or more NMR sensors, data of earth formation fluid; and a data processing unit communicatively coupled with the data acquisition tool, the data processing unit comprising a second memory storing instructions that, when executed by a data processor, cause the data processor to perform operations comprising obtaining, from the acquired data, at least one fully polarized state echo train ($E_{FR}$) and at least one partially polarized state echo train burst ($E_{PR}$), wherein the at least one $E_{PR}$ includes a plurality of partially polarized bins and a plurality of fully polarized bins, inverting the at least one $E_{PR}$ to obtain an apparent transverse relaxation time ($T_{2app}$) distribution, wherein the $T_{2app}$ distribution includes fully polarized state echo train data and partially polarized state echo train data, truncating the $T_{2app}$ distribution by discarding the partially polarized state echo train data, completing a forward model of the $E_{PR}$ to obtain at least one additional echo train burst ($E_{FR\_B}$), performing a second inversion of the data set, and determining, at the data processor, earth formation fluid properties based on the second inversion.

Statement 32: An apparatus is disclosed according to Statement 31, wherein the earth formation fluid properties are used to determine one of a bound water location, a movable water location, a fluid type, or a fluid volume.

Statement 33: An apparatus is disclosed according to Statement 31 or Statement 32, wherein the at least one $E_{FR}$ is obtained by the following equation:

$$E_{FR}(i, t_E, t_{W_{FR}}) = \sum_{m=1}^{M} E_{0,m} e^{-i\frac{t_{E_j}}{T_{2,m}}}.$$

Statement 34: An apparatus is disclosed according to Statements 31-33, wherein the at least one $E_{PR}$ is obtained by the following equation:

$$E_{PR}(i, t_E, t_W) = \sum_{n=1}^{\mu} E_{0,n} e^{-i\frac{t_E}{T_{2,n}}} + \sum_{n=\mu+1}^{N} E'_{0,n} e^{-i\frac{t_E}{T_{2,n}}}$$

where $\mu$ is a number of fully polarized bins.

Statement 35: An apparatus is disclosed according to Statements 31-34, wherein completing the forward model further comprises generating at least one $E_{FR\_B}$ having only fully polarized bins using the following equation:

$$E_{FP\_B}(i, t_E, t_W) = \sum_{n=1}^{\mu} E_{0,n,est} e^{-i\frac{t_E}{T_{2,n}}}$$

where $E_{0,n,est}$ is the estimated bin porosity corresponding to $T_{2,n}$.

Statement 36: An apparatus is disclosed according to Statements 31-35, wherein the second inversion further comprises inverting the at least one $E_{FR}$ and the at least one $E_{FR\_B}$ simultaneously to obtain a $T_2$ distribution and a total porosity level.

Statement 37: An apparatus is disclosed according to Statements 31-36, wherein two or more $E_{FR\_B}$ are obtained, and wherein the second inversion further comprises inverting the at least one $E_{FR}$ and the two or more $E_{FR\_B}$ sequentially to obtain a $T_2$ distribution and a total porosity level.

Statement 38: An apparatus is disclosed according to Statements 31-37, wherein when more than one $E_{FR\_B}$ is obtained, each $E_{FR\_B}$ is forward modeled independently and the second inversion is applied to $E_{FR}$ and each $E_{FR\_B}$ concurrently.

Statement 39: An apparatus is disclosed according to Statements 31-38, wherein the wait time ($t_w$) of the at least one $E_{PR}$ is shorter than the $t_w$ of the at least one $E_{FR}$.

Statement 40: An apparatus is disclosed according to Statements 31-39, wherein the at least one $E_{PR}$ has a first number of echoes and the at least one $E_{FR}$ has a second number of echoes, wherein the second number of echoes is greater than the first number of echoes.

Statement 41: An apparatus is disclosed according to Statements 31-40, wherein the at least one $E_{FR\_B}$ has the same number of echoes as the at least one $E_{PR}$.

Statement 42: An apparatus is disclosed according to Statements 31-40, wherein the at least one $E_{FR\_B}$ has a different number of echoes than the at least one $E_{PR}$.

Statement 43: An apparatus is disclosed according to Statements 31-42, wherein the at least one $E_{FR\_B}$ has the same $t_E$ value as the at least one $E_{PR}$.

Statement 44: An apparatus is disclosed according to Statements 31-42, wherein the at least one $E_{FR\_B}$ has a different $t_E$ value than the at least one $E_{PR}$.

Statement 45: An apparatus is disclosed according to Statements 31-44, further comprising a display communicatively coupled to the data processing unit and rendering the determined earth formation fluid properties.

The embodiments shown and described above are only examples. Even though numerous characteristics and advantages of the present technology have been set forth in the foregoing description, together with details of the structure and function of the present disclosure, the disclosure is illustrative only, and changes may be made in the detail, especially in matters of shape, size and arrangement of the parts within the principles of the present disclosure to the full extent indicated by the broad general meaning of the terms used in the attached claims. It will therefore be appreciated that the embodiments described above may be modified within the scope of the appended claims.

What is claimed:

1. A method for determining earth formation rock and fluid properties comprising:
    providing a data acquisition tool, the data acquisition tool comprising:
        one or more nuclear magnetic resonance (NMR) sensors, a data acquisition processor communicatively coupled with the one or more NMR sensors, and a first memory communicatively coupled with the data acquisition processor;

lowering the data acquisition tool to a desired location within a wellbore;

receiving, at the data acquisition tool, data of earth formation fluid;

transmitting the acquired data to a data processing unit communicatively coupled with the data acquisition tool, the data processing unit comprising a data processor and a second memory;

obtaining, from the acquired data, at least one fully polarized state echo train ($E_{FR}$) and at least one partially polarized state echo train burst ($E_{PR}$), wherein the at least one $E_{PR}$ includes a plurality of partially polarized bins and a plurality of fully polarized bins;

inverting the at least one $E_{PR}$ to obtain an apparent transverse relaxation time ($T_{2app}$) distribution, wherein the $T_{2app}$ distribution includes fully polarized state echo train data and partially polarized state echo train data;

truncating the $T_{2app}$ distribution by discarding the partially polarized $T_{2app}$ bins;

completing a forward model of the $E_{PR}$ to obtain at least one additional echo train burst ($E_{FR\_B}$) having only fully polarized bins;

performing a second, simultaneous inversion on the at least one $E_{FR}$ and the at least one $E_{FR\_B}$ obtained from the forward model, the second inversion providing a $T_2$ distribution and a total porosity level;

determining, at the data processor, earth formation fluid properties based on the second inversion.

2. The method of claim 1, wherein the at least one $E_{FR}$ is obtained by the following equation:

$$E_{FR}(i, t_E, t_{W_{FR}}) = \sum_{m=1}^{M} E_{0,m} e^{-i\frac{t_{E_j}}{T_{2,m}}},$$

where:
$E_{FR}$ is at least one fully polarized state echo train,
$E_{0,m}$ is the bin porosity,
$t_{E_j}$ is echo time, and
$T_{2,m}$ is the transverse relaxation time when m=1, . . . , μ.

3. The method of claim 1, wherein the at least one $E_{PR}$ is obtained by the following equation:

$$E_{PR}(i, t_E, t_W) = \sum_{n=1}^{\mu} E_{0,n} e^{-i\frac{t_E}{T_{2,n}}} + \sum_{n=\mu+1}^{N} E'_{0,n} e^{-i\frac{t_E}{T_{2,n}}}$$

where:
$E_{PR}$ is at least one partially polarized state echo train,
$E_{0,n}$ is the bin porosity,
μ is a number of fully polarized bins,
$E'_{0,n}$ is the partially polarized bin porosity,
$t_E$ is echo time, and
$T_{2,n}$ is the transverse relaxation time when n=1, . . . , μ.

4. The method of claim 1, wherein completing the forward model further comprises generating the at least one $E_{FR\_B}$ using the following equation:

$$E_{FP\_B}(i, t_E, t_W) = \sum_{n=1}^{\mu} E_{0,n,est} e^{-i\frac{t_E}{T_{2,n}}}$$

where:
$E_{FR\_B}$ is at least one additional echo train burst,
$E_{0,n,est}$ is the estimated bin porosity,
$t_E$ is echo time, and
$T_{2,n}$ is the transverse relaxation time when n=1, . . . , μ.

5. The method of claim 1, wherein a wait time ($t_w$) of the at least one $E_{PR}$ is shorter than a $t_w$ of the at least one $E_{FR}$.

6. The method of claim 1, wherein the at least one $E_{PR}$ has a first number of echoes and the at least one $E_{FR}$ has a second number of echoes, wherein the second number of echoes is greater than the first number of echoes.

7. The method of claim 1, further comprising displaying the earth formation fluid properties on a display screen communicatively coupled with the data processing unit.

8. A system comprising:
a data acquisition tool disposed in a wellbore, the data acquisition tool comprising:
one or more nuclear magnetic resonance (NMR) sensors communicatively coupled to a data acquisition processor, and a first memory communicatively coupled to the data acquisition processor, the first memory storing instructions that, when executed by the data acquisition processor, cause the data acquisition processor to perform operations comprising:
receiving, at the data acquisition tool, data of earth formation fluid, and
transmitting, at the data acquisition processor, the acquired data;
a data processing unit communicatively coupled with the data acquisition tool, the data processing unit comprising a second memory storing instructions that, when executed by a data processor, cause the data processor to perform operations comprising:
receiving, from the data acquisition processor, the acquired data,
obtaining, from the acquired data, at least one fully polarized state echo train ($E_{FR}$) and at least one partially polarized state echo train burst ($E_{PR}$), wherein the at least one $E_{PR}$ includes a plurality of partially polarized bins and a plurality of fully polarized bins,
inverting the at least one $E_{PR}$ to obtain an apparent transverse relaxation time ($T_{2app}$) distribution, wherein the $T_{2app}$ distribution includes fully polarized state echo train data and partially polarized state echo train data,
truncating the $T_{2app}$ distribution by discarding the partially polarized $T_{2app}$ bins,
completing a forward model of the $E_{PR}$ to obtain at least one additional echo train burst ($E_{FR\_B}$) having only fully polarized bins,
performing a second, simultaneous inversion on the at least one $E_{FR}$ and the at least one $E_{FR\_B}$ obtained from the forward model, the second inversion providing a $T_2$ distribution and a total porosity level, and
determining, at the data processor, earth formation fluid properties based on the second inversion.

9. The system of claim 8, wherein the at least one $E_{FR}$ is obtained by the following equation:

$$E_{FR}(i, t_E, t_{W_{FR}}) = \sum_{m=1}^{M} E_{0,m} e^{-i\frac{t_{E_j}}{T_{2,m}}},$$

where:
$E_{FR}$ is at least one fully polarized state echo train,
$E_{0,m}$ is the bin porosity,
$t_{E_j}$ is echo time, and
$T_{2,m}$ is the transverse relaxation time when m=1, ..., μ.

10. The system of claim 8, wherein the at least one $E_{PR}$ is obtained by the following equation:

$$E_{PR}(i, t_E, t_W) = \sum_{n=1}^{\mu} E_{0,n} e^{-i\frac{t_E}{T_{2,n}}} + \sum_{n=\mu+1}^{N} E'_{0,n} e^{-i\frac{t_E}{T_{2,n}}}$$

where:
$E_{PR}$ is at least one partially polarized state echo train,
$E_{0,n}$ is the bin porosity,
μ is a number of fully polarized bins,
$E'_{0,n}$ is the partially polarized bin porosity,
$t_E$ is echo time, and
$T_{2,n}$ is the transverse relaxation time when n=1, ..., μ.

11. The system of claim 8, wherein completing the forward model further comprises generating the at least one $E_{FR\_B}$ using the following equation:

$$E_{FP\_B}(i, t_E, t_W) = \sum_{n=1}^{\mu} E_{0,n,est} e^{-i\frac{t_E}{T_{2,n}}}$$

where:
$E_{FR\_B}$ is at least one additional echo train burst,
$E_{0,n,est}$ is the estimated bin porosity,
$t_E$ is echo time, and
$T_{2,n}$ is the transverse relaxation time when n=1, ..., μ.

12. The system of claim 8, wherein a wait time ($t_w$) of the at least one $E_{PR}$ is shorter than a $t_w$ of the at least one $E_{FR}$.

13. The system of claim 8, wherein the at least one $E_{PR}$ has a first number of echoes and the at least one $E_{FR}$ has a second number of echoes, wherein the second number of echoes is greater than the first number of echoes.

14. The system of claim 8, further comprising a display communicatively coupled to the data processing unit and rendering the determined earth formation fluid properties.

15. An apparatus comprising:
a data acquisition tool comprising:
one or more nuclear magnetic resonance (NMR) sensors;
a data acquisition processor communicatively coupled with the one or more NMR sensors; and
a first memory storing instructions that, when executed by the data acquisition processor, cause the data acquisition processor to perform operations comprising acquiring, at the one or more NMR sensors, data of earth formation fluid; and
a data processing unit communicatively coupled with the data acquisition tool, the data processing unit comprising:
a second memory storing instructions that, when executed by a data processor, cause the data processor to perform operations comprising:
obtaining, from the acquired data, at least one fully polarized state echo train ($E_{FR}$) and at least one partially polarized state echo train burst ($E_{PR}$), wherein the at least one $E_{PR}$ includes a plurality of partially polarized bins and a plurality of fully polarized bins,
inverting the at least one $E_{PR}$ to obtain an apparent transverse relaxation time ($T_{2app}$) distribution, wherein the $T_{2app}$ distribution includes fully polarized state echo train data and partially polarized state echo train data,
truncating the $T_{2app}$ distribution by discarding the partially polarized $T_{2app}$ bins,
completing a forward model of the $E_{PR}$ to obtain at least one additional echo train burst ($E_{FR\_B}$) having only fully polarized bins,
performing a second, simultaneous inversion on the at least one $E_{PR}$ and the at least one $E_{FR\_B}$ obtained from the forward model, the second inversion providing a $T_2$ distribution and a total porosity level, and
determining, at the data processor, earth formation fluid properties based on the second inversion.

16. The apparatus of claim 15, wherein the at least one $E_{FR}$ is obtained by the following equation:

$$E_{FR}(i, t_E, t_{W_{FR}}) = \sum_{m=1}^{M} E_{0,m} e^{-i\frac{t_{E_j}}{T_{2,m}}},$$

where:
$E_{FR}$ is at least one fully polarized state echo train,
$E_{on}$ is the bin porosity,
$t_{E_j}$ is echo time, and
$T_{2,m}$ is the transverse relaxation time when m=1, ..., μ.

17. The apparatus of claim 15, wherein the at least one $E_{PR}$ is obtained by the following equation:

$$E_{PR}(i, t_E, t_W) = \sum_{n=1}^{\mu} E_{0,n} e^{-i\frac{t_E}{T_{2,n}}} + \sum_{n=\mu+1}^{N} E'_{0,n} e^{-i\frac{t_E}{T_{2,n}}}$$

where:
$E_{PR}$ is at least one partially polarized state echo train,
$E_{0,n}$ is the bin porosity,
μ is a number of fully polarized bins,
$E'_{0,n}$ is the partially polarized bin porosity,
$t_E$ is echo time, and
$T_{2,n}$ is the transverse relaxation time when n=1, ..., μ.

18. The apparatus of claim 15, wherein completing the forward model further comprises generating the at least one $E_{FR\_B}$ using the following equation:

$$E_{FP\_B}(i, t_E, t_W) = \sum_{n=1}^{\mu} E_{0,n,est} e^{-i\frac{t_E}{T_{2,n}}}$$

where:
$E_{FR\_B}$ is at least one additional echo train burst,
$E_{0,n,est}$ is the estimated bin porosity,
$t_E$ is echo time, and
$T_{2,n}$ is the transverse relaxation time when n=1, ..., μ.

19. The apparatus of claim 15, wherein a wait time ($t_w$) of the at least one $E_{PR}$ is shorter than a $t_w$ of the at least one $E_{FR}$.

20. The apparatus of claim 15, further comprising a display communicatively coupled to the data processing unit and rendering the determined earth formation fluid properties.

* * * * *